United States Patent [19]

Mehra

[11] Patent Number: 4,526,594

[45] Date of Patent: Jul. 2, 1985

[54] PROCESS FOR FLEXIBLY REJECTING SELECTED COMPONENTS OBTAINED FROM NATURAL GAS STREAMS

[75] Inventor: Yuv R. Mehra, Odessa, Tex.

[73] Assignee: El Paso Hydrocarbons Company, Odessa, Tex.

[21] Appl. No.: 532,005

[22] Filed: Sep. 14, 1983

Related U.S. Application Data

[63] Continuation-in-part of Ser. No. 374,270, May 3, 1982, Pat. No. 4,421,535, and Ser. No. 507,564, Jun. 24, 1983, Pat. No. 4,511,381.

[51] Int. Cl.³ .................................................. F25J 3/02
[52] U.S. Cl. ............................................ 62/17; 55/73; 55/76
[58] Field of Search ............... 62/17, 20, 23, 9, 11; 55/68, 73, 76

[56] References Cited

U.S. PATENT DOCUMENTS

| | | | |
|---|---|---|---|
| 2,139,375 | 12/1938 | Mills et al. | 23/2 |
| 2,290,957 | 7/1942 | Hachmuth | 196/8 |
| 2,649,166 | 8/1953 | Porter et al. | 183/115 |
| 2,849,371 | 8/1958 | Gilmore | 196/2 |
| 3,287,262 | 11/1966 | Jones | 208/341 |
| 3,362,133 | 1/1968 | Kutsher et al. | 55/44 |
| 3,594,985 | 7/1971 | Ameen et al. | 55/73 |
| 3,664,091 | 5/1972 | Hegwer | 55/29 |
| 3,737,392 | 6/1973 | Ameen et al. | 252/364 |
| 3,837,143 | 9/1974 | Sutherland et al. | 55/32 |
| 3,877,893 | 4/1975 | Sweny et al. | 55/32 |
| 4,252,548 | 2/1981 | Markbreiter et al. | 62/17 |
| 4,276,057 | 6/1981 | Becker et al. | 50/40 |
| 4,302,220 | 11/1981 | Volkamer et al. | 55/32 |
| 4,318,715 | 3/1982 | Chou | 55/44 |
| 4,345,918 | 8/1982 | Meissner | 55/38 |

OTHER PUBLICATIONS

Sweny, John W., "High CO₂-High H₂S Removal with Selexol Solvent", Mar. 17-19, 1980, 59th Annual GPA Convention, Houston, Texas.

*Primary Examiner*—Frank Sever
*Attorney, Agent, or Firm*—Depaoli & O'Brien

[57] ABSTRACT

A continuous process is described for treating a raw inlet natural gas stream to produce: (a) a liquid $C_2+$ hydrocarbon product having a composition that is selectively adjustable to substantially any selected degree, as the market price for each individual hydrocarbon liquid falls below its fuel price, by selectively rejecting a consecutive molecular weight string of $C_2-C_4$ components and then returning the desirable price component or components to the liquid products stream and (b) a sweet, dry residue natural gas stream of pipeline quality which includes the rejected $C_2$, $C_3$, and/or $C_4$ hydrocarbon components.

47 Claims, 3 Drawing Figures

PROCESS FOR FLEXIBLY REJECTING SELECTED COMPONENTS OBTAINED FROM NATURAL GAS STREAMS

RELATED APPLICATIONS

This is a continuation-in-part of co-pending application Ser. No. 374,270, filed May 3, 1982, of Yuv R. Mehra, entitled "Process for Recovery of Natural Gas Liquids From a Sweetened Natural Gas Stream" now U.S. Pat. No. 4,421,535 and of co-pending application Ser. No. 507,564, filed June 24, 1983, of Yuv R. Mehra, entitled "Process for Extracting Natural Gas Liquids From Natural Gas Streams With Physical Solvents" now U.S. Pat. No. 4,511,381.

BACKGROUND OF THE INVENTION

1. Field of the Invention

This invention relates to the recovery of hydrocarbons from a natural gas stream and further relates to separating ethane and higher boiling hydrocarbons from the methane in a natural gas stream. It more specifically relates to supplying specific market needs for hydrocarbons by selective recovery of ethane, propane, or ethane plus propane from a stream of lower molecular weight hydrocarbons that have been selectively rejected from a stream of $C_2+$ hydrocarbons recovered from a natural gas stream.

2. Review of the Prior Art

Numerous processes have been used to extract liquids from natural gas streams. These processes include oil absorption, refrigerated oil absorption, simple refrigeration, cascaded refrigeration, Joule-Thompson expansion, and cryogenic turbo-expansion.

In summary, the oil absorption, refrigerated oil absorption, simple refrigeration, and cascaded refrigeration processes operate at the pipeline pressures, without letting down the gas pressure, but the recovery of desirable liquids (ethane plus heavier components) is quite poor, with the exception of the cascaded refrigeration process which has extremely high operating costs but achieves good ethane and propane recoveries. The Joule-Thompson and cryogenic expander processes achieve high ethane recoveries by letting down the pressure of the entire inlet gas, which is primarily methane (typically 80-85%), but recompression of most of the inlet gas is quite expensive.

In all of the above processes, the ethane plus heavier components are recovered in a specific configuration determined by their composition in the raw natural gas stream and by equilibrium at the key operating conditions of pressure and temperature within the process. Flexibility of recovery, independently of such composition and equilibrium, is not possible.

Under poor economic conditions when, for example, ethane price as petrochemical feedstock is less than its equivalent fuel price and when the propane price for feedstock usage is attractive, the operator of a natural gas liquid extraction plant is consequently limited as to operating choice because he is unable to minimize ethane recovery and maximize propane recovery in response to market conditions.

The refrigeration process which typically recovers 80% of the propane also typically requires the recovery of 35% of the ethane. In order to boost propane recovery to the 95+% level, cascaded refrigeration, Joule-Thompson, or cryogenic turbo expander processes would have to be used while simultaneously boosting the ethane recovery to 70+% at a considerably larger capital investment.

Similarly, when the ethane price as petrochemical feedstock is greater than its fuel value while propane price as propane feedstock is unattractive, none of the above-mentioned processes allow an operator to selectively recover ethane while rejecting propane.

Extraction processes are available that employ liquids other than hydrocarbon oils for removal of acidic components, including $H_2S$ and $CO_2$, and water. These liquids comprise propylene carbonate, N-methyl pyrrolidone, glycerol triacetate, polyethyleneglycol dimethyl ether (DMPEG), triethylolamine, tributyl phosphate, and gamma butyrolacetone.

U.S. Pat. Nos. 3,362,133, 3,770,622, 3,837,143, 4,052,176, and 4,070,165 teach various prior art processes for extracting acidic components, heavier hydrocarbons, or water from natural gas streams.

As presented at the 50th Annual Gas Processors Association Convention, Mar. 17-19, 1980, in a paper entitled "High $CO_2$—High $H_2S$ Removal with SELEXOL Solvent" by John W. Sweny, the relative solubility in DMPEG of $CO_2$ over methane is 15.0 while that of propane is 15.3. The relative solubility in DMPEG of $H_2S$ over methane is 134 versus 165 for hexane in DMPEG. The relative solubilities in DMPEG of iso and normal butanes and of iso and normal pentanes are in between those of propane and $H_2S$. These data indicate that if $CO_2$ and $H_2S$ are present in a natural gas stream which contains $C_2+$ heavier hydrocarbons that are desirable for petrochemical industry feedstocks, substantial quantities of $C_2+$ hydrocarbons will be lost with $CO_2$ and $H_2S$ vent streams when a sour natural gas stream is treated with DMPEG.

Sweet natural gas is usually saturated with water at its ambient temperature which may have a range of 75°-120° F., so that its water content may vary from 20 pounds to more than 50 pounds per million standard cubic feet. However, difficulties are frequently met while pumping such natural gas unless the water content is reduced to a value of less than 12 pounds, preferably less than 7 pounds, of water per million standard cubic feet of natural gas. In terms of dew point, a natural gas having a dew point of 30° F., preferably 20° F. or lower, is generally considered safe for transportation in a pipeline. Dehydration can be carried out under a wide range of pressures from 15 to 5000 psig, but it is usually carried out at pipeline pressures of 500-1500 psig and generally near 1000 psig.

There has nevertheless existed a need for a process wherein $C_2+$ hydrocarbons and water could be simultaneously removed to any selected degree without also extracting hydrocarbons of lower molecular weight, such as methane.

There has additionally existed a need for a process wherein any natural gas, from very sour to entirely sweet, could be handled by the same equipment while simultaneously dehydrating the gas and recovering the heavier hydrocarbons.

These needs have been met by the process described in the parent application, Ser. No. 06/507,564, filed June 24, 1983, which is fully incorporated herein by reference. This process produces a liquid hydrocarbon product having a composition which is selectively versatile rather than fixed, as in prior art processes. In consequence, the composition of its hydrocarbon product can be readily adjusted in accordance with market conditions so that profitability of the absorption operation can be maximized at all times and on short notice.

Such versatility is achieved by flexibility in certain operating conditions and by use of certain additional steps that are not used in the prior art. These conditions and steps are listed as follows, in order of importance:

(1) varying the flow rate of the solvent with respect to flow rate of the natural gas stream;

(2) varying the flashing pressure for one or more of the successive flashing stages;

(3) recycling the flashed $C_1+$ undesirable gases to the extraction column; and (4) rejecting selected components of the liquid product, viz., methane (demethanizing), methane plus ethane (de-ethanizing), methane, ethane, and propane (depropanizing), or methane, ethane, propane, and butanes (debutanizing) in a stripping column for the liquid product by:

(a) varying the pressure in the column, and (b) varying the temperature at the bottom of the column.

When an operator is changing process conditions to produce a new liquid product mix in accordance with the needs of the market, he must have all four process steps available for consideration. He must consider each of the steps in the order listed, but he need not necessarily change all of them. For some natural gas streams, solvent flow variation and recycling in addition to demethanizing is adequate, for example. However, for most natural gas streams, optimum efficiency is obtained when all five of the preceding conditions and steps are utilized. It is thereby extremely easy, for example, to recover $99+\%$ of propane and less than 2% of ethane without any additional investment or to recover $99+\%$ of the butanes and less than 2% of the ethane and propane without any additional investment.

"Demethanizing" refers strictly to removal of methane from the liquid product entering the demethanizer. When ethane is additionally removed, such removal may herein be referred to as de-ethanizing; when propane is also removed, such removal may herein be identified as depropanizing; and when butanes are further removed, such removal may herein be described as debutanizing. Nevertheless, the generic term used herein for removal of $C_1$, $C_1+C_2$, $C_1+C_2+C_3$, or $C_1+C_2+C_3+C_4$'s is demethanizing or stripping, and, unless otherwise qualified, this term is to be understood as encompassing any one of these four removal possibilities.

However, daily changes in market conditions may also cause the price of a single liquid hydrocarbon heavier than ethane to drop below its fuel price so that this hydrocarbon should be selectively rejected, but there is presently no way of doing so without also rejecting all components of lower molecular weight. For example, if the price of ethane is below its fuel value, it can be rejected with the methane, as taught in the parent application, but if the price of propane is below its fuel value while the price of ethane is above its fuel value, no method exists for separating these hydrocarbons.

Therefore, for all components heavier than ethane, there exists a need for selectively rejecting any one or two selected hydrocarbons of consecutive molecular weight that are heavier than another recoverable and desirable hydrocarbon which may include ethane. As a practical matter, such hydrocarbons which need to be selectively rejectable are propane, the butanes, and propane plus the butanes.

SUMMARY OF THE INVENTION

The object of this invention is to provide an extraction process for selectively removing $C_2+$, $C_3+$, $C_4+$, or $C_5+$ hydrocarbon components from a natural gas stream by contact with a physical solvent, according to an extremely flexible wide range of hydrocarbon recoveries but preferably while achieving extremely high hydrocarbon recoveries, for selectively rejecting therefrom the $C_1$–$C_3$, $C_1$–$C_4$, or $C_2$–$C_4$ components of consecutive molecular weight, and for selectively recovering therefrom the $C_2$, the $C_3$, or the $C_2+C_3$ components.

Another object is to provide a process for forming a residue natural gas of pipeline quality consisting only of undesirable hydrocarbon components of a natural gas stream to any selected degree and producing a liquid hydrocarbon product consisting only of desirable hydrocarbon components to any selected degree.

A further object is to provide a process for forming a residue natural gas to be used for burning purposes with a Btu content within a specified range.

An additional object is to provide a process for forming a residue natural gas to be used as a petrochemical feedstock with a specified composition, such as two or three components of a specified ratio, in which methane is the inert diluent.

According to these objects and the principles of this invention, a process is herein provided that is useful when changes in the market prices for individual hydrocarbons in liquid form cause the market price for an individual hydrocarbon liquid to fall below its fuel price. Such prices change on a daily basis. Accordingly, it becomes advantageous to be able to extract all of the hydrocarbon liquids while rejecting and returning to the residue gas line one or more hydrocarbons that are priced below their fuel value. The extraction plant can thereby be operated at optimum profit levels at all times.

In order to make such a rejection, a second extractor unit, a single flash unit, and a splitting unit, herein termed a de-ethanizer, are additionally needed. A hydrocarbon stream, having a significantly different composition and consisting of desirable lighter hydrocarbon components, such as ethane ($C_2$), and undesirable heavier hydrocarbon components, such as propane ($C_3$), from the inlet natural gas stream, is extracted with a solvent stream in the second extractor at selected solvent flow rates. Depending upon the rate of circulation of the solvent, undesirable lighter hydrocarbons such as $C_1$ or $C_1+C_2$ containing minor amounts of desirable hydrocarbons leave the second extractor as an overhead stream, are compressed, and are cooled before returning to the first extraction unit. Depending upon the recovery objectives, these gases may bypass the first extractor unit and return directly to the residue gas pipeline. The bottom stream from the extractor, again depending upon the rate of circulation of the solvent, comprises $C_2+C_3$ or $C_2+C_3+C_4$ hydrocarbons along with the solvent. These are fed to a single flash tank. The overhead stream from the flash tank is compressed, cooled, condensed, and fed to the de-ethanizer. The bottoms stream from the flash tank, consisting primarily of extraction solvent, is sent to the solvent regenerator unit.

Since the gaseous feed stream to the second extracting unit contains significantly less amounts of methane than the inlet natural gas stream being fed through the first extracting unit, the relative partial pressures of the heavier hydrocarbons in the second extractor feed are considerably higher. This situation causes the solvent requirements for the second extracting unit to be significantly lower (in the range of 0.001 to 0.2 gallons per standard cubic foot of second extractor feed) than the solvent requirements for the first extracting unit (0.005 to 0.5 gallons per standard cubic foot of inlet natural gas as first extractor feed), provided both first and second extracting units are operating at the same pressure.

However, there is no external requirement for the pressure in the second extractor to be the same as in the first extractor since the first extractor generally operates at residue gas pipeline pressures. A minimal pressure of 300 psia is essential for the second extracting unit. Since compression of gases is relative quite expensive, it may be preferred to operate the second extracting unit as close to 300 psia as possible and consequently forfeit the advantage of concentration of heavier hydrocarbons in the second extractor feed which produces higher partial pressures. In other words, it may be preferred to use higher solvent feed rates to the second extracting unit, similar to the requirements for the first extracting unit of 0.005 to 0.5 gallons per standard cubic foot of extracting feed. In general, therefore, and depending upon the pressures within the extractors, the solvent flow rates to the first and second extractors can vary from 0.001 to 0.5 gallons/scf of feed.

The de-ethanizer or splitter is equipped with a reboiler and a recirculating line for heating its contents. When the main demethanizer for the gas extraction is being operated as a depropanizer, thereby indicating that propane is an undesirable component, the splitter is being operated as a de-ethanizer and produces $C_2$ as its overhead stream and $C_3$ as its bottoms stream. When the main demethanizer is being operated as a debutanizer, thereby indicating that butanes are undesirable components, the splitter is being operated as a de-ethanizer and produces $C_2$ or as a depropanizer and produces $C_3$ or $C_2+C_3$ as its overhead stream. The bottoms stream, when the splitter is operating as de-ethanizer, consists of $C_3$ and $C_4$ but is composed of $C_4$ when the splitter is being operated as a depropanizer. The bottoms streams are sent to the residue gas line, and the overhead streams are sent to the liquid products line.

The relationship of this invention to the invention of the parent application is illustrated in the accompanying Table I. The first four cases or situations summarize the capabilities described in the parent application for selectively extracting $C_{2}+$ hydrocarbons and particularly for selectively not extracting or extracting and then rejecting consecutively lower molecular weight hydrocarbons, viz., $C_1+C_2$, $C_1+C_2+C_3$, or $C_1+C_2+C_3+C_4$. It should be understood, however, that $C_4$ refers to both iso and normal butanes, $C_5$ refers to both iso and normal pentanes, and the like. It should be understood that minor amounts of other desirable or undesirable components may be present which are not shown in Table I. The components shown under various streams are those which are predominant.

TABLE I

| Case No. | I | II | III | IV | V | VI | VII | VIII | Pipelines |
|---|---|---|---|---|---|---|---|---|---|
| Reject Objectives | $C_1$ | $C_1, C_2$ | $C_1, C_2, C_3$ | $C_1, C_2, C_3, C_4$ | $C_1, C_3$ | $C_1, C_4$ | $C_1, C_2, C_4$ | $C_1, C_3, C_4$ | |
| First Extracting, Multiple Flashing, and Demethanizing | | | | | | | | | |
| Unextracted Hydrocarbons from First Extracting | $C_1$ | $C_1, C_2$ | $C_1, C_2, C_3$ | $C_1, C_2, C_3, C_4$ | $C_1$ | $C_1$ | $C_1, C_2$ | $C_1$ | 12 |
| Stripping or De-ethanizing Bottoms as Product | $C_2+$ | $C_3+$ | $C_4+$ | $C_5+$ | $C_4+$ | $C_5+$ | $C_5+$ | $C_5+$ | 95 |
| Stripping or Demethanizing Overhead as Rejects | $C_1$ | $C_1, C_2$ | $C_1, C_2, C_3$ | $C_1, C_2, C_3, C_4$ | $C_1, C_2, C_3$ | $C_1, C_2, C_3, C_4$ | $C_2, C_3, C_4$ | $C_1, C_2, C_3, C_4$ | 92 |
| Second Extracting, Single Flashing, and De-ethanizing | | | | | | | | | |
| Combined Flashed-Off Gases + Demethanizing Rejects | — | — | — | — | $C_1, C_2, C_3$ | $C_1, C_2, C_3, C_4$ | $C_2, C_3, C_4$ | $C_1, C_2, C_3, C_4$ | 137 |
| Unextracted Hydrocarbons from Second Extracting | — | — | — | — | $C_1$ | $C_1$ | $C_2$ | $C_1$ | 152 |
| Single-Flashed Gases | — | — | — | — | $C_2, C_3, C_4$ | $C_2, C_3, C_4$ | $C_3, C_4$ | $C_2, C_3, C_4$ | 162 |
| Splitting or De-ethanizing Bottoms as Rejects | — | — | — | — | $C_3$ | $C_4$ | $C_4$ | $C_3, C_4$ | 175 |
| Splitting or De-ethanizing Overhead as Selected Products | — | — | — | — | $C_2$ | $C_2, C_3$ | $C_3$ | $C_2$ | 172 |
| Products | | | | | | | | | |
| Combined Demethanizing Bottoms + De-ethanizing Overhead to form Liquid Hydrocarbon Products | $C_2+$ | $C_3+$ | $C_4+$ | $C_5+$ | $C_2, C_4+$ | $C_2, C_3, C_5+$ | $C_3, C_5+$ | $C_2, C_5+$ | 84 |
| Combined First and Second Unextracted Hydrocarbons + De-ethanizing Bottoms to Form Residue Natural Gas | $C_1$ | $C_1, C_2$ | $C_1, C_2, C_3$ | $C_1, C_2, C_3, C_4$ | $C_1, C_3$ | $C_1, C_4$ | $C_1, C_2, C_4$ | $C_1, C_3, C_4$ | 19 |

The last four cases or situations in the table summarize the capabilities of this invention for further processing the rejected hydrocarbons from the first demethanizing unit plus any flashed-off gases that are neither recycled to the first extracting unit nor sent to the demethanizing unit. This combined feed is extracted in the second extracting unit with the same physical solvent as used in the first extracting unit. The unextracted hydrocarbons, which are methane or methane plus ethane, containing minor amounts of desirable hydrocarbons such as ethane or propane, are sent to the first extracting unit, and the rich solvent stream from the second extracting unit is sent to the single flashing unit. The extracted and flashed-off hydrocarbons are compressed, cooled, and condensed, and are then sent to the de-ethanizing unit which has a reboiler. The operating pressure and bottoms temperature of the de-ethanizing unit can be varied at will. Its overhead is the selected liquid hydrocarbon product and its bottoms is the selected reject having a liquid hydrocarbon value below its fuel value.

The continuous process of this invention produces from an inlet natural gas stream: (a) a liquid hydrocarbon product of a selected composition, which is selectively adjustable to substantially any selected degree in accordance with market conditions and includes ethane, propane, ethane plus propane, or propane plus butane, along with C$_5$+ components, and (b) a residue natural gas stream of pipeline quality which selectively and simultaneously includes propane, butane, or propane plus butane in inverse proportion to the quantities of each of these hydrocarbons in the liquid hydrocarbon product. This process comprises the following steps:

A. selectively removing a stream of hydrocarbons that are primarily heavier than methane from the natural gas stream;

B. selectively rejecting a consecutively lowest molecular weight portion of the extracted stream, this rejected portion comprising, as its heaviest component, the propane or the butanes;

C. selectively removing ethane, propane, or ethane plus propane from the rejected portion;

D. combining the remainder of the rejected portion from Step C with the remainder of the natural gas stream of Steps B and A, the first remainder comprising the propane, the butane, or the propane plus butane, to form the residue natural gas stream, and E. combining the ethane, the propane, or the ethane plus propane from Step C with the remainder of the extracted stream from Steps A and B to form the liquid hydrocarbon product.

Step A is performed by the following steps:

A. extracting the water and the hydrocarbons that are primarily heavier than methane from the natural gas stream with a physical solvent at pipeline pressures and at a solvent flow rate sufficient to produce rich solvent containing the water, a selected C$_1$+ mixture of hydrocarbons, and the remainder of the natural gas stream;

B. successively flashing the rich solvent in a plurality of flashing stages at successively selected decreasing pressures to produce a plurality of successive C$_1$+ gas fractions, having successively lower methane contents, and successive liquid mixtures of the water, the solvent, and mixtures of hydrocarbons having successively lower methane contents; and C. regenerating the liquid mixture from the last stage of the flashing stages to produce the physical solvent for the extracting.

The first Step B, for rejecting the consecutively lowest molecular weight portion of the extracted stream, is performed by utilizing at least one of the following operational procedures as disclosed in the parent application:

A. selectively varying the solvent flow rate with respect to the flow rate of the natural gas stream during the extracting step to adjust the composition of the rich solvent stream relative to selected components of the group consisting of ethane, propane, iso and normal butanes, and components heavier than butanes;

B. selectively varying the flashing pressures of the successive flashing stages in order to adjust the compositions of the successive gas fractions and of the successive liquid mixtures relative to the selected components;

C. recycling at least the first of the successive flashed C$_1$+ gas fractions to the extracting step in order to extract maximum quantities of the hydrocarbons heavier than methane; and D. demethanizing at least the last of the successive C$_1$+ gas fractions, in order to produce the desired remainder of the extracted stream, by:

(1) selectively varying the pressure of the demethanizing, and (2) selectively varying the bottoms temperature of the demethanizing.

The selective removing of ethane, propane, or ethane plus propane from the lowest molecular weight rejected portion, according to the first Step C, comprises the following steps:

A. selectively extracting the rejected portion in the second extracting unit to produce a gas stream, selected from the group consisting of methane and methane plus ethane, and a second rich solvent stream, consisting of the physical solvent and at least two of the highest molecular weight components of the rejected portion;

B. flashing the second rich solvent stream to produce an overhead stream consisting of all extracted hydrocarbon components and a bottom physical solvent stream; and C. de-ethanizing the overhead stream in the splitter to produce:

(1) the ethane, the propane, or the ethane plus propane as an overhead product stream; and (2) the propane, the butane, or the propane plus butane as a bottoms stream for combining with the remainder of the natural gas stream to produce the residue natural gas stream.

The physical solvent used in the second extracting is a portion of the regenerated physical solvent of the second Step C. The portion of the physical solvent used in the second extracting is combined with the liquid mixture remaining from the plurality of flashing stages as set forth in the second Step C, these combined solvents being regenerated according to the second Step C.

The at least last of the successive C$_1$+ gas fractions for the second Step D is compressed, condensed, and cooled to become feed for the demethanizing. This feed is heated to a selected bottoms temperature and at a selected pressure to remove an off-gas mixture therefrom, the off-gas mixture comprising essentially all of the methane and selected amounts of ethane, propane, and butanes that are present in the feed to form the consecutively lowest molecular weight portion of the extracted stream that is selectively rejected according to the first Step B.

The physical solvent is selective toward ethane and heavier hydrocarbon components of the inlet natural gas stream with respect to methane, such that the relative volatility of methane over ethane is at least 5.0 and the hydrocarbon loading capacity, defined as solubility of ethane in solvent, is at least 0.25 standard cubic feet of ethane per gallon of solvent.

This physical solvent is selected from the group consisting of dialkyl ethers of polyalkylene glycol, N-methyl pyrrolidone, dimethyl formamide, propylene carbonate, sulfolane, and glycol triacetate. The solvent is preferably selected from the group consisting of dimethyl ether of polyethylene glycol, dimethyl ether of polypropylene glycol, dimethyl ether of tetramethylene glycol, and mixtures thereof, and the solvent most preferably is dimethyl ether of polyethylene glycol containing 3–10 ethylene units and having a molecular weight of 146 to 476.

The regenerating is done by supplying heat to a reboiler to produce an overhead vaporous stream which is cooled, settled, pumped, and returned to the regenerator after disposing of excess waste water therefrom.

Typically, the selected solvent flow rate ranges between 0.005 to 0.5 gallon per standard cubic foot of the natural gas stream, and the selected flashing pressures of the successive flashing stages vary between 1300 psia and 2 psia. The bottoms temperature of the demethanizing varies between 0° F. and 300° F.

This process can be operated to remove $C_2+$ hydrocarbon liquids from the inlet natural gas stream and to reject the methane therein as the selected degree, whereby the liquid product of the demethanizing comprises up to 98% of the ethane content, all heavier hydrocarbons that are in the inlet natural gas stream, and less than 2% of the methane content therein as the selected degree (Case I in Table I), as discussed in the parent application.

On the other hand, this process can be operated to remove $C_3+$ hydrocarbon liquids from the natural gas stream and to reject the methane and ethane therein as the selected degree, the demethanizing of the second Step D being operated as a first de-ethanizing (Case II in Table I). The liquid product of the first de-ethanizing thereby comprises up to 99% of the propane content, all heavier hydrocarbons that are in the natural gas stream, and less than 2% of the ethane content therein as the selected degree, as is also taught in the parent application.

This process can also be operated to recover $C_4+$ hydrocarbon liquids and to reject methane, ethane, and propane therein as the selected degree, the demethanizing of the second Step D being operated as a first depropanizing which produces a liquid product comprising approximately 100% of the butanes, all heavier hydrocarbons that are in the natural gas stream, and less than 2% of ethane and propane therein as the selected degree, as disclosed in the parent application (Case III in Table I).

Furthermore, the process can be operated to recover $C_5+$ hydrocarbon liquids from the natural gas stream and to reject the ethane, propane, and butane therein as the selected degree, the demethanizing being operated as a debutanizing step which produces a liquid product comprising approximately 100% of the pentanes, all heavier hydrocarbons that are in the natural gas stream, and less than 2% of ethane, propane, and butanes as the selected degree (Case IV in Table I).

The ethane and propane can be substantially completely rejected in the extracting and in the multiple flashing stages. Alternatively, they can be partially rejected in the extracting, further rejected in the multiple flashing stages, and substantially completely rejected after passing through the demethanizing operation; the first one or two off-gas streams are typically recycled to the extracting, and the last one or two off-gas streams are sent to the demethanizing. As a second alternative, they can be rejected only slightly, if at all, in the extracting, moderately rejected in the flashing stages, and mostly rejected in the demethanizing; all of the off-gas streams from the multiple flashing stages may then be sent to the demethanizing. Either alternative can be used for the selective rejection of propane according to this invention because a fairly small part of the methane and 98% of the ethane and propane are available as an extract feed stream.

Selective rejection of propane, according to Case V in Table I, occurs by operating demethanizing as depropanizing and by countercurrently extracting the extract feed stream, containing $C_1$, $C_2$, and $C_3$, with the physical solvent in the second extracting, whereby the $C_1$ is removed and returned to the first extracting. The rich solvent is then singly flashed, producing $C_2$ and $C_3$ as an overhead stream which is de-ethanized, producing $C_2$ as the overhead product and $C_3$ as the bottoms product which is combined with the residue natural gas from the first extracting.

According to Case VI in Table I, the extract feed stream consists essentially of $C_1$, $C_2$, $C_3$, and $C_4$ hydrocarbons because the demethanizing is operated as debutanizing. After the second extracting, $C_1$ is the unextracted hydrocarbon which is combined with the residue natural gas, and $C_2$, $C_3$, and $C_4$ form the flashed-off gas stream which is depropanized in the splitter to form $C_4$ as the bottoms stream which is rejected to the first residue gas pipeline and $C_2+C_3$ as the overhead product stream which is combined with the bottoms stream from the debutanizing.

According to Case VII in Table I, wherein $C_5+$ hydrocarbon liquids form the debutanizing bottoms, the first extracting and the multiple flashing stages are operated so that, with recycling of the first two off-gas streams to the first extracting, essentially all of the $C_1$ and much of the $C_2$ are not extracted and are in the residue natural gas stream. The remaining $C_2$, the $C_3$, and the $C_4$ form the extract feed stream for the second extracting. $C_2$ forms the overhead stream which is recycled to the first extracting. $C_3$ and $C_4$ are extracted in the second extracting and sent to the depropanizing in the splitter to produce $C_3$ as the overhead stream which is combined with the $C_5+$ hydrocarbon liquids to form the liquid hydrocarbon product. The bottoms stream from the depropanizing in the splitter is $C_4$ which is combined with the residue natural gas stream from the first extracting.

According to Case VIII in Table I, wherein $C_5+$ hydrocarbon liquids also form the debutanizing bottoms, the first extracting and the multiple flashing stages are operated and the off-gas recycling is arranged so that essentially all of the $C_2+$ components are extracted in addition to some $C_1$. The second extracting feed stream consists of $C_1$, $C_2$, $C_3$, and $C_4$. The overhead from the second extracting is $C_1$, the single-flashed gases are $C_2$, $C_3$, and $C_4$, the de-ethanizing overhead from the splitter is $C_2$, and the de-ethanizing bottoms are $C_3$ and $C_4$. The combined residue natural gas stream therefore contains $C_1$, $C_3$, and $C_4$, and the combined liquid hydrocarbon products stream contains $C_2$ and $C_5+$ hydrocarbons.

The residue natural gas can also be a valuable product. When consumed for heating purposes, such as in power plants and homes, the Btu content may be quite important, and a customer may specify a gas feed having a Btu content within certain ranges. Additionally, other customers, such as petrochemical plants, might desire an inlet feed having two or three components in which one is methane as an inert diluent, with nitrogen being an acceptable additional diluent, to provide a desired liquid or vapor hourly space velocity. This process enables the residue natural gas to be provided with its Btu content within a desired range, such as 950 to 974 Btu/SCF, or with its composition according to a customer's order, such as 70/30 of $C_2/C_3$ or 50/50 $C_2/C_3$ or 25/75 $C_1/C_4$.

DESCRIPTION OF THE PREFERRED EMBODIMENTS

Figure 1:
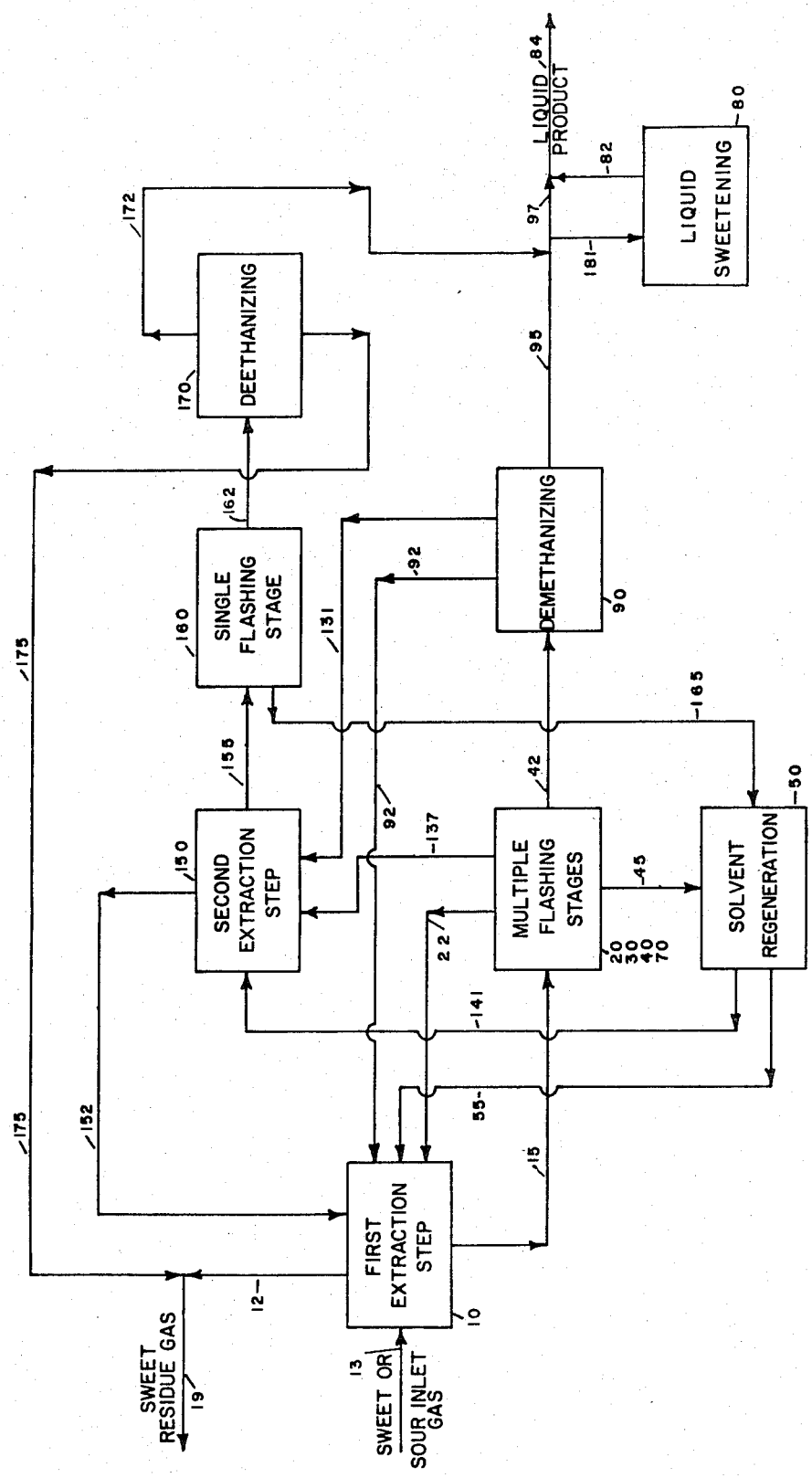
FIG. 1 is a combined flow sheet which schematically shows the interrelationship of the basic operations of the parent application and of this invention.

The summarized schematic flowsheet of FIG. 1 combines the process of the parent invention, as given in Cases I through IV in Table I, that produces a recycle stream of consecutive lower molecular weight hydrocarbons, selectively from $C_1$ through $C_4$, and the process of this invention, as given in Cases V through VIII in Table I, that extracts from this recycle stream any $C_1$ and $C_2$ for recycling to the first extracting and then removes $C_2$, $C_3$, or $C_2+C_3$ for combining with the liquid hydrocarbon products from the demethanizing.

As broadly shown in FIG. 1, sweet or sour inlet natural gas 13 enters first extraction step 10 to which solvent in line 55 and recycled materials in lines 22, 92, and 152 are also fed. Unextracted gas leaves through line 12, and rich solvent leaves through line 15, entering multiple flashing stages 20,30,40,70 through line 15. Flashed materials pass to demethanizing 90 through line 42, to second extraction step 150 through line 137, and to first extraction step 10 through line 22. The solvent flows from multiple flashing stages 20,30,40,70 to solvent regeneration 50 through line 45, and additional solvent enters through line 165. Regenerated solvent returns to first extraction unit 10 through line 55 and to second extraction unit 150 through line 141.

The overhead or rejected hydrocarbons of consecutively lower molecular weight leave demethanizing 90 through line 92 to first extraction unit 10 and through line 131 to second extraction unit 150. The bottoms streams of $C_2+$, $C_3+$, $C_4+$, or $C_3+$ hydrocarbons leaves demethanizing 90 through line 95.

The unextracted hydrocarbons pass from second extraction unit 150 to first extraction unit 10 through line 152. The rich solvent stream flows to single flashing stage 160 through line 155. Stripped solvent passes to solvent regeneration unit 50 through line 165.

The singly flashed-off hydrocarbons pass from single flashing stage 160 to de-ethanizing 170 through line 162. The overhead stream of $C_2$, $C_3$, or $C_2+C_3$ hydrocarbons passes through line 172 to join the bottoms stream of liquid hydrocarbons in line 95 to form stream 97 which leaves the process through line 84 as liquid product. If the inlet natural gas in line 13 is sour, however, the combined liquid hydrocarbons pass through line 181 to liquid sweetening 80 and thence, as a sweet liquid hydrocarbons product, through line 82 to line 84 as the liquid product of the process. The bottoms from de-ethanizing 170 is rejected through line 175 to combine with unextracted hydrocarbons in line 12 from first extracting 10 to form sweet residue gas in line 19.

Figure 2:
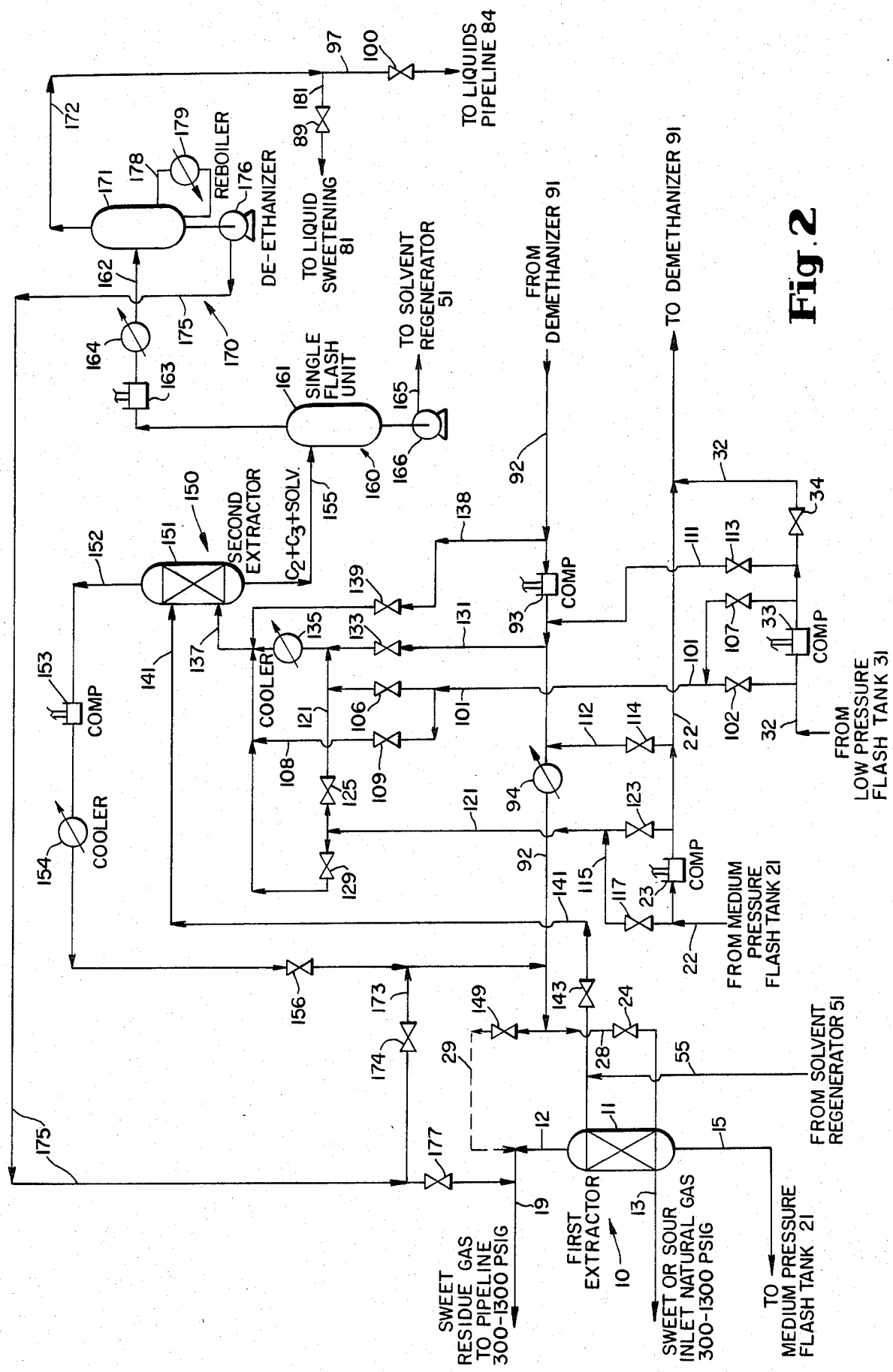
FIG. 2 is a more detailed flow sheet which shows the invention of this application in detail, plus the extracting of the natural gas, as described in the parent application, and the alternatively usable lines for the flashed-off and demethanized feed streams to the second extracting.

The amplified flowsheet of the improved hydrocarbon separation process of this invention that is shown in FIG. 2 is the same as the flowsheet of FIG. 1 as to its main details. However, the varied flow paths of the flashed-off gases from multiple flashing stages 20,30 and of the gases from demethanizer 90 are illustrated in much greater detail. In addition, valves, coolers, compressors, pumps, reboilers, and the like are shown and identified.

The flow system for feeding the flashed-off gases and the demethanized overhead to second extractor 151 comprises a collection line 137 which receives the contents of lines 138,131,101, and 121. Lines 138 and 131 are connected to line 92, the overhead discharge line from demethanizer 91, before and after compressor 93, respectively.

Line 32, the overhead discharge line from low pressure flash tank 31, is connected to line 101, which has a valve 102, upstream of compressor 33 and is also connected to line 101, downstream of compressor 93, through a line having valve 107. It is then connected to line 111 having a valve 113. Line 32 has its own valve 34 and joins line 22 for discharge to demethanizer 91. Line 111 is connected to line 92, downstream of compressor 93, so that it can bypass demethanizer 91 and second extractor 151 while returning to first extractor 11.

Depending upon the operating pressure of second extracting unit 150, the gases from stream 92 may feed second extractor 151 via line 131. Line 131 has valve 133 and cooler 135 and discharges into line 127. Depending upon the operating pressures of tank 31 and second extractor 151, line 101 may be used to directly pass the gases from stream 32 to line 127 via line 108 having valve 109.

Line 22, the overhead discharge line from medium pressure flash tank 21, has a compressor 23 and is connected to line 115, having valve 117, upstream of compressor 23 and to line 121, having valve 123, downstream thereof. Line 22 is also connected to line 112, having valve 114, which discharges into line 92 upstream of cooler 94. Line 22 can also discharge into demethanizer 91.

Line 121 has additional valve 125 and discharges into line 131, upstream of cooler 135. Bypass line 127, having valve 129, is connected to line 121, upstream of valve 125, and discharges into line 137. Bypass line 108, having valve 109, is connected to line 101, upstream of valve 106, and discharges into line 127. The remaining portion of FIG. 2 is identical to FIG. 3 and is described with respect to FIG. 3.

Figure 3:
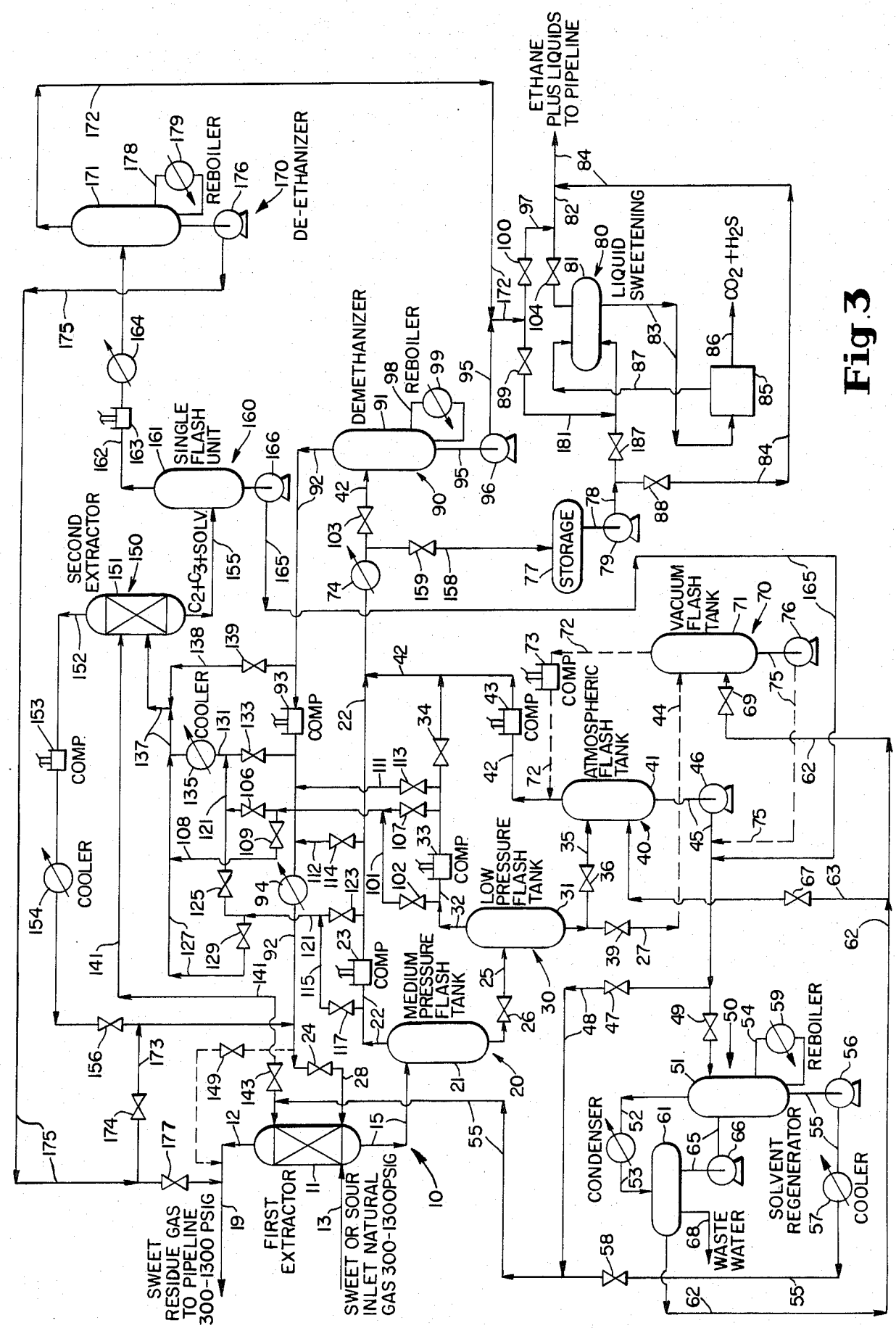
FIG. 3 is a thoroughly detailed flowsheet which applies to both inventions and schematically illustrates a varied combination of preferred embodiments for treating both sweet and sour natural gases, having any water content up to saturation.

The process shown schematically in FIG. 3 comprises a first extraction (absorption) unit 10, a medium pressure flash unit 20, a low pressure flash unit 30, an atmospheric flash unit 40, a vacuum flash unit 70, a regenerator unit 50, a demethanizer unit 90, a liquid sweetening unit 80, a second extraction unit 150, a single flash unit 160, and a de-ethanizer unit (splitter) 170 which is selectively utilizable as a de-ethanizer unit or a depropanizer unit. A multiplicity of lines, compressors, coolers, and valves are available for sending each of the flashed and liquid streams to these units in any desired succession in order to extract any hydrocarbon and/or to reject any specific hydrocarbon or group of hydrocarbons from $C_1$ through $C_4$.

When inlet stream 13 is a sweet natural gas at 300–1300 psig, it has generally been sweetened by countercurrent passage to an aqueous amine solution which has removed sour materials, including $H_2S$ and $CO_2$, while saturating the natural gas with water. If the natural gas is sour, but relatively dry, it may be desirable to extract the sour gas and sweeten the liquid product in liquid sweetening unit 80 because the load on regenerator unit 50 is considerably lessened.

Extractor 11 is maintained at about 20°–120° F., preferably at about 70°–80° F. Solvent is fed through line 55 at a rate sufficient to reduce the water content of the sweet natural gas leaving through line 12 to less than 12 pounds per million standard cubic feet and preferably to less than 7 pounds per million standard cubic feet. Under these conditions, the ethane and other hydrocarbon components of greater molecular weight in line 12 are reduced to a very low value. By altering the amount of solvent entering through line 55, the proportion of ethane to the predominant methane may be varied at will, but the solvent ratio is usually at 0.005 to 0.5 gallon of solvent per standard cubic foot of inlet natural gas, whether sweet or sour.

The rich solvent in line 15 enters medium pressure flash tank 21 from which primarily methane and some heavier hydrocarbons are discharged through line 22. A mixture of solvent, hydrocarbon components, and water is dicharged through line 25 and valve 26 and enters low pressure flash tank 31 from which a mixture of additional methane and some heavier hydrocarbons is dicharged through line 32. A mixture of solvent, remaining methane, ethane, heavier hydrocarbons, and water is discharged through line 35 and valve 36. It should be understood that the lower the solvent flow rate, the less $C_2+$ hydrocarbons are removed from the inlet natural gas. It should be further understood that the more $C_2+$ hydrocarbons are in the inlet natural gas, the less methane is extracted at a given solvent flow rate. Furthermore, the lower the flashing pressure, the more methane is removed in each flashing stage. However, the number of flashing stages that is used is generally a function of the inlet natural gas pressure. The reason therefor is that the higher the inlet pressure, the more stages can be used to create a smaller pressure drop between each stage and consequently a higher overall efficiency. If the inlet natural gas is, for example, at 1200 psig, four flashing stages are desirable. But if the inlet natural gas is at a low to moderate pressure such as 600 psig, three flashing stages are adequate. In general, the smaller the pressure drop between flashing stages, the less the flashed amount of desirable hydrocarbons from the solvent and thereby the less recycle of the desirable components to the first extracting unit 11.

Solvent regeneration unit 50 comprises solvent regenerator 51, reboiler 59 with circulating line 54, overhead discharge line 52 and condenser 53, settler 61, waste water discharge line 68, water return line 65, pump 66, and hydrocarbon vapor return line 62.

When a mixture of solvent, water, and trace quantities of hydrocarbons is discharged from atmospheric flash tank 41 or vacuum flash tank 71 through line 45 and pump 46 or line 75 and pump 76, respectively, and sent to solvent regenerator unit 50, reboiler 59 heats solvent, taken from the bottom of regenerator 51 and passing through line 54, in order to supply heat to the regenerator. The vaporized mixture of trace hydrocarbons and water passes from the top of regenerator 51 through line 52, is condensed in condenser 53, and enters settler 61 from which water is discharged through line 65 and pump 66 to return to regenerator 51 as reflux. Waste water is discharged from settler 61 through line 68. The hydrocarbon vapors from settler 61 leave through line 62 and enter atmospheric flash tank 41 through line 63 and valve 67 or enter vacuum flash tank 71 through line 62 and valve 69. Water-free solvent is discharged from regenerator 51 through line 55 and pump 56, cooled in cooler 57, and passed through valve 58 to extractor 11. If the inlet natural gas entering the system through line 13 does not contain water, the solvent in line 48, when valve 49 is closed, can bypass regenerator unit 50 through line 48 and valve 47 to join solvent return line 55 to extractor 11.

As is apparent from FIG. 3, overhead streams in lines 22 and 32 can bypass demethanizer unit 90 for direct recycle to extractor 11 through line 112 and valve 114 and line 111 and valve 113 via line 92. Alternatively, these streams in lines 22 and 32 can join line 42 which has earlier received the atmospheric flash stream and/or the overhead vacuum flash stream in line 72, for passing through cooler 74 and valve 103 to enter demethanizer 91.

Demethanizer unit 90 comprises demethanizer 91, reboiler 99, circulating line 98, overhead discharge line 92, bottoms discharge line 95, and pump 96. The temperature at the bottom of demethanizer 91 is controlled by providing heat through reboiler 99 and returning the heated bottom liquid through line 98 to demethanizer 91. The bottom liquid meets the product specifications as to undesirable components (such as methane, ethane, propane, butanes, $CO_2$, $H_2S$, and the like) and leaves the process through line 95 and pump 96 for pipeline shipments via valve 100, line 97, line 82, and line 84.

However, if acidic components have not previously been removed, liquid sweetening unit 80 is needed. Liquid sweetening unit 80 comprises a main contactor 81 and stripping unit 85. If a process arrangement does not require demethanizer unit 90, a liquid storage tank 77 is utilized to feed the liquid sweetening unit 80 through line 158 and valve 159 to storage tank 77 and then through line 78, pump 79, and valve 187. If a demethanizer unit 90 is utilized in the process, the sour liquids are fed from demethanizer 91 through line 95, line 172, valve 89, and line 181 to line 78. Amines contactor 81 produces a sweet product, passing through valve 104 and line 82, which consists essentially of ethane plus heavier hydrocarbon liquids for pipeline shipment. The identity of these heavier hydrocarbons depends upon previous de-ethanizing, depropanizing, or debutanizing treatment, in addition to demethanizing treatment. The sour amine stream in line 83 is stripped in unit 85, producing a $CO_2$ and $H_2S$ stream leaving through line 86 with negligble content of hydrocarbons. The sweet amines stream returns to contactor 81 through line 87. If the liquid product meets the required specifications without utilizing demethanizer unit 90 and the liquids are sweet, the liquid product may bypass liquid sweetening unit 80 via line 84 and valve 88.

Extraction unit 10, medium pressure flash unit 20, low pressure flash unit 30, atmospheric flash unit 40, vacuum flash unit 70, and demethanizer unit 90, with recirculating lines for methane-rich streams in line 92, plus liquid sweetening unit 80 and solvent regenerator unit 50, are sufficient, with their accessory compressors, coolers, valves, and lines, to provide sweet dry residue gas to a pipeline through line 12 and $C_2+$ liquids, $C_3+$ liquids, $C_4+$ liquids, or $C_5+$ liquids through line 95, with $C_2$-$C_4$ hydrocarbons being selectively rejected and discharged as a portion of the sweet, dry residue gas in line 12. However, when market prices change for individual hydrocarbons in liquid form, so that the market price for an individaul hydrocarbon liquid falls below its fuel price, it becomes advantageous to be able to extract all of the hydrocarbon liquids while rejecting and returning one or more liquids that are priced below their fuel value. All that can be done with the equipment in FIG. 3 that has been thus far described is to reject a selected lower molecular weight hydrocarbon along with all hydrocarbons of consecutively lower molecular weight, as a string or grouping of lower molecular weight hydrocarbons. What is needed are an apparatus and a method for separating one or more hydrocarbons that are desirable liquid hydrocarbon products from the remainder of the rejected string.

In order to make such a separation, second extractor unit 150, single flash unit 160, and de-ethanizer unit 170 are additionally needed pieces of apparatus. Extractor unit 150 receives a gaseous hydrocarbon stream in line 137 and solvent in line 141 with valve 143 from line 55. Methane or ethane (Case VII in Table I) leaves as an overhead stream in line 152, is compressed by compressor 153, and is cooled by heat exchanger 154 before passing through valve 156 and entering line 92 for recycle to first extractor 11 via line 28 and valve 24.

The bottom stream in line 155, depending upon the rate of circulation of the solvent, comprises $C_2+C_3$ hydrocarbon liquids or $C_2+C_3+C_4$ hydrocarbon liquids which are fed to single flash tank 161 from which an overhead stream passes through line 162, compressor 163, and heat exchanger 164 to enter de-ethanizer 171. The bottom stream in line 165 is then pumped by pump 166 to solvent regenerator unit 50 through line 45.

The hydrocarbon stream in line 162 enters de-ethanizer 171 which is equipped with a reboiler 179 and a recirculating line 178 for heating the contents thereof. The overhead stream is ethane if the unit is being operated as a deethanizer; alternatively, the overhead stream is propane or ethane plus propane if the unit is being operated as a depropanizer. The overhead products from line 172 are combined with products from line 95 to leave the process via line 84. Correspondingly, the bottoms stream in line 175, pumped by pump 176, consists of propane or propane plus butanes if the unit is being operated as a de-ethanizer or butane if the unit is being operated as a depropanizer. The hydrocarbon stream in line 175 passes through valve 177 to join line 12 containing residue natural gas. Line 173 and valve 174 may be used to recycle contents of line 175 to first extractor 11 via line 152.

Cooler 135 for compressed gases bypassing cooler 94 is an essential part of the intermediate hydrocarbon rejection system formed by liquid extraction unit 150, single flash unit 160, and de-ethanizer unit 170 in addition to numerous lines and valves for controlling the flow and selectively bypassing various units of the entire treatment system, as previously described in relation to FIG. 2.

Depending upon the recovery objectives, the recycle gases from the process in line 92 may bypass first extractor 11, via line 29 and valve 149, and go directly to residue gas line 12.

The flexibility of this treatment system for selectively stripping desired hydrocarbon liquids from an inlet natural gas stream, sweet or sour and having any water content up to saturation, with a physical solvent is illustrated in the following examples.

EXAMPLE 1

Case I

As described in the parent application and shown in FIG. 3, an ethane recovery plant is put into operation to treat one million standard cubic feet per day (1 MMSCFD) of sweetened natural gas for 95% ethane recovery. The composition of the natural gas entering extractor 11 of extractor unit 10 is as follows:

| Component | MOL % |
|---|---|
| Nitrogen | 2.01 |
| Methane | 80.62 |
| Ethane | 9.69 |
| Propane | 4.83 |
| Iso-Butane | 0.50 |
| N—Butane | 1.45 |
| Iso-Pentane | 0.30 |
| N—Pentane | 0.37 |
| Hexane Plus | 0.22 |
|  | 100.00 |
| Water Content | 169 lbs/MMSCFD inlet gas |
| Inlet Pressure | 625 psia |
| Inlet Temperature | 120° F. |

The sweetened natural gas stream in line 13 enters first extractor 11 near its bottom. A recycle stream in line 28 also enters the extractor near the bottom. The combined gases from the streams in lines 13 and 28 flow upward in the extractor where they are contacted by the lean solvent stream in line 55 flowing downwards. The molar ratio of solvent to the fresh feed stream in line 13 is of the order of 1.36:1.00. Ethane and heavier liquids present in the inlet gas stream are selectively absorbed and removed from the extractor through line 15. The remaining natural gas leaves the extractor through line 12 which is primarily composed of nitrogen, methane, and small amounts of ethane, depending upon the desirable recoveries of ethane. Virtually all of the propane and heavier components are removed from stream 13. The stream in line 15 contains about 2.1 times as many moles of methane as moles of ethane.

In order to remove methane from recovered hydrocarbons while conserving energy consumption, the pressure of the stream in line 15 is let down from 625 psia to 400 psia in medium pressure flash tank 21 wherein the vapor stream in line 22, rich in methane (about 88 MOL % methane), is separated from the liquid stream in line 25 which contains about 30% less methane and about 94% of the ethane present in stream 15. Stream 22 is compressed from 400 psia to 630 psia for recycle back to first extractor via lines 112,92,28.

In order to further reduce the amount of methane which is associated with ethane, the liquid pressure is reduced from 400 psia to 300 psia in low pressure flash tank 31. Here the stream in line 32, consisting of about 86 MOL % methane, is separated from the liquid stream in line 35 which contains about 1.19 moles of methane per mole of ethane and has about 51% less methane than the amount of methane present in the stream in line 15. Vapors leaving via the stream in line 32 are compressed to 630 psia for recycle to first extractor 11 via lines 111, 92,28.

In order to separate all hydrocarbon components from the solvent, the pressure of the liquid stream in line 35 is reduced from 300 psia to 5 psia by valve 39 in line 27 to vacuum flash tank 71. The hydrocarbon vapors leaving tank 71 via the stream in line 72 are compressed to 400 psia in compressors 73 and 43 and cooled to 20° F. in condenser 74 to condense ethane plus heavier hydrocarbons. Some methane also gets condensed and is stripped by demethanizer 91. The demethanized liquid product meeting specifications leaves the process via lines 95,97,84. The stripped methane leaves demethanizer 91 via line 92 and is compressed to 630 psia for recycle to first extractor 11. The combined streams in lines 112, 111, and 92 are cooled to about 120° F. and recycled to first extractor 11 via line 28.

Depending upon the ethane recovery requirements, it may or may not be necessary to recycle the stream in line 28 to the first extractor. Instead, this stream can bypass the first extractor and leave the plant through line 29 by joining the residue gas stream in line 12. The amount of methane that is present in the rich solvent stream in line 15 depends upon the partial pressures of desirable hydrocarbon components in the inlet natural gas stream.

The liquid stream in line 75 leaving vacuum flash tank 71 contains about 1.5 MOL % hydrocarbons and water, with the rest being the solvent. This stream is pumped into solvent regenerator 51 where contained water and hydrocarbons are separated overhead. The solvent regenerator operates typically at about 20 psia. The solvent is heated to about 300° F. to completely remove water from the solvent in the solvent regenerator and is cooled to about 120° F. before returning it to the extractor as the regenerated solvent stream in line 55. However, the water content of the solvent stream in line 55 can be 2-15 wt. % without causing any detrimental effect on the performance of the first extractor.

The water is separated from the hydrocarbon vapors in column overhead accumulator 61 and is used as reflux through line 65 for solvent regenerator 51. Excess water leaves the process through line 68. The hydrocarbon vapors are recycled under its pressure via line 62 to vacuum flash tank 71. However, in a process wherein an atmospheric flash tank 41 is used, the hydrocarbon vapors may be routed via lines 62 and 63 to atmospheric flash tank 41 instead of to vacuum flash tank 71.

The operation of the process as described in Example 1 can be more clearly understood by study of the compositions of the various streams in pound-mols per hour (LB-MOLS/HR). Eleven components of 15 streams are given in the following Tables II and III.

TABLE II
MATERIAL BALANCE FOR ILLUSTRATIVE EXAMPLE

| Components Lb-Mols/Hr | Stream in Line No. | | | | | | |
|---|---|---|---|---|---|---|---|
| | 13 | 55 | 12 | 15 | 28 | 22 | 25 |
| Nitrogen | 2.22 | — | 2.22 | 0.11 | 0.11 | 0.07 | 0.04 |
| Methane | 88.48 | — | 88.26 | 25.76 | 25.54 | 7.69 | 18.07 |
| Ethane | 10.63 | — | 0.54 | 12.09 | 2.00 | 0.75 | 11.34 |
| Propane | 5.30 | — | Trace | 5.60 | 0.30 | 0.15 | 5.45 |
| Iso-Butane | 0.55 | — | — | 0.57 | 0.02 | 0.01 | 0.56 |
| N—Butane | 1.59 | — | — | 1.63 | 0.04 | 0.02 | 1.61 |
| Iso-Pentane | 0.33 | — | — | 0.33 | — | — | 0.33 |
| N—Pentane | 0.41 | — | — | 0.41 | — | — | 0.41 |
| Hexane Plus | 0.29 | — | — | 0.29 | — | — | 0.29 |
| Water | 0.39 | — | — | 0.39 | — | — | 0.39 |
| Solvent | — | 150.0 | — | 150.00 | — | — | 150.00 |
| TOTAL, LB-MOLS HR | 110.19 | 150.00 | 91.02 | 197.18 | 28.01 | 8.69 | 188.49 |

TABLE III
MATERIAL BALANCE FOR ILLUSTRATIVE EXAMPLE

| Components Lb-Mols/Hr | Stream in Line No. | | | | | | | |
|---|---|---|---|---|---|---|---|---|
| | 32 | 35 | 72 | 75 | 92 | 95 | 68 | 62 |
| Nitrogen | 0.02 | 0.02 | — | — | 0.02 | — | — | — |
| Methane | 5.39 | 12.68 | 12.68 | 0.09 | 12.46 | 0.22 | — | 0.09 |
| Ethane | 0.71 | 10.63 | 10.63 | 0.44 | 0.54 | 10.09 | — | 0.44 |
| Propane | 0.15 | 5.30 | 5.30 | 0.51 | Trace | 5.30 | — | 0.51 |
| ISO-Butane | 0.01 | 0.55 | 0.55 | 0.09 | — | 0.55 | — | 0.09 |
| N—Butane | 0.02 | 1.59 | 1.59 | 0.31 | — | 1.59 | — | 0.31 |
| ISO-Pentane | — | 0.33 | 0.33 | 0.10 | — | 0.33 | — | 0.10 |
| N—Pentane | — | 0.41 | 0.41 | 0.15 | — | 0.41 | — | 0.15 |
| Hexane Plus | — | 0.29 | 0.29 | 0.13 | — | 0.29 | — | 0.13 |
| Water | — | 0.39 | — | 0.39 | — | — | 0.39 | Trace |
| Solvent | — | 150.00 | — | 150.00 | — | — | Trace | — |
| TOTAL, LB-MOLS/HR | 6.30 | 182.19 | 31.78 | 152.21 | 13.02 | 18.78 | 0.39 | 1.82 |

It is apparent from these tables that about 30% of the 25.76 pound-mols/hr of methane that is dissolved in the solvent stream in line 15 is returned to first extractor 11 in line 22, about 21% is returned in line 32, and about 48% is returned in line 92. With respect to the 12.09 pound-mols/hr of ethane that leave in the solvent stream in line 15, about 6.2% is returned to first extractor 11 in line 22, 5.9% is returned to first extractor 11 in line 32, 4.5% is returned in line 92, and 83.4% leaves in the product stream in line 95. With respect to the 5.60 pound-mols/hr of propane in the stream in line 15, 2.7% returns in line 22, and 2.7% returns in line 32 to first extractor 11 via line 28 while 94.6% leaves in the product stream in line 95.

Without employing demethanizer unit 90, it is clear that about half of the methane can become part of the product stream in line 84. Nonetheless, economic considerations, based upon product specifications, may easily obviate a need for demethanizer unit 90. Moreover, other design considerations may be important. For example, if the proportion of $C_2+$ hydrocarbons is unusually high, the amount of methane absorbed in the solvent is proportionately less.

If only propane plus heavier hydrocarbons are desired as a liquid product, such as for Case II for example, up to 98% of ethane and about 1% of propane entering the process through line 13 could leave the process via line 12 while easily recovering 99% of propane with about 2% of ethane from the stream in line 13 as components of the stream in line 95 containing 100% of the butanes and heavier hydrocarbons. These desirable recoveries can be achieved by changing the operating conditions, such that the solvent-to-fresh feed molar ratio would be significantly lowered to about 0.95 and the pressure in the medium pressure tank would be around 250 psia, the low pressure tank would operate at about 150 psia, while the demethanizer would operate as a de-ethanizer at about 275 psia.

Similarly, by changing the solvent flow rate to the first extractor, changing the pressures in the subsequent flashing stages, and adjusting the pressure and temperature in the demethanizing unit, propane or butanes could be rejected to any selected degree in order to produce $C_4+$ or $C_5+$ liquid products.

EXAMPLE 2

Extraction of $C_2$ and $C_4+$ Liquids From Sweet Inlet Natural Gas and Rejection of $C_3$ (Case V)

The process, as described under Example 1, is operated quite similarly to remove $C_2+$ hydrocarbons from the inlet natural gas, with the exception that only the vapors from flash tank 21 are recycled directly to first extractor 11 via lines 112 and 28. All other streams either flow directly to line 137 or via demethanizer 91 to line 137. The operating pressure of flash tank 31 is lowered to about 200 psia to flash larger amounts of higher boiling hydrocarbons, especially ethane and propane, and the pressure and temperature in demethanizer unit 90 are varied so that larger amounts of ethane and propane pass through line 92 as overhead while demethanizer unit 90 is operated as a depropanizer.

Line 137, entering second extractor 151, consequently contains $C_1+C_2+C_3$. The ratio of solvent flow, through line 141 and valve 143, to gas flow, through line 137, is sufficient, varying from 0.001 to 0.2 gallons per SCF, that the overhead stream from second extractor 151 contains primarily methane with some ethane; it passes through line 152/compressor 153/cooler 154/valve 156/line 92/line 28 for recycle to first extractor 11. The stream in line 155 contains solvent plus $C_2$ and $C_3$.

The overhead stream from single flash tank 161 flows as follows: line 162/compressor 163/cooler and condenser 164/de-ethanizer 171. The bottoms stream is entirely solvent and flows through line 165 and pump 166 to line 45 and thence to regenerator unit 50.

In de-ethanizer 171, pressure and temperature are controlled by flow recirculating line 178 and reboiler 179 so that ethane leaves as overhead through line 172 to join line 95 while propane leaves through line 175, pump 176, and valve 177 to join line 12. The combined liquid hydrocarbon product from lines 172 and 95 is therefore $C_2$ and $C_4+$ and leaves the process via lines 97 and 84 since the gases are sweet and the product meets specifications.

EXAMPLE 3

Extraction of $C_2$, $C_3$, and $C_5+$ Liquids From Sweet Inlet Natural Gas and Rejection of Butanes (Case VI)

The process is operated as in Example 2 except that demethanizer 91 is operated as a debutanizer, so the stream in line 92 consists of $C_1$, $C_2$, $C_3$, and $C_4$, the stream in line 152 consists of $C_1$, and the stream in line 155 consists of $C_2$, $C_3$, $C_4$. De-ethanizer 171 is also operated as a depropanizer, the stream in line 175 consists of $C_4$, and the stream in line 172 consists of $C_2$ and $C_3$, thereby augmenting the $C_5+$ liquid product passing through line 95/pump 96/line 172/line 97/valve 100/line 82 to liquids pipeline 84.

Even though only a few schematic arrangements have been illustrated and described hereinbefore, it should be recognized that the process steps are important and that they can be arranged in a multitude of combinations consistent with the operational objectives and given market conditions. The invention process is extremely flexible and cannot be limited to the schematic arrangements described in the examples or even as shown in the drawings. As an illustration, the flashed-off gases from medium-pressure tank 21 and even from low-pressure tank 31 can be recycled directly to first extractor 11 through line 22/compressor 23/line 112/valve 114/line 92/cooler 94/valve 24/line 28 to extractor 11 and through line 32/compressor 33/line 111/valve 113/line 92/cooler 94/valve 24/line 28 to extractor 11, respectively. Such recycle from the first two flash tanks is indeed highly preferred for Case VII, as shown in Table I.

It is very important to note that the high ethane plus heavier hydrocarbon recoveries are achieved by clean separation of components in demethanizer unit 90 and de-ethanizer unit 170 and by closing the loop around the process by means of recycling; as such, any $C_2+$ components leaving in the overhead streams of medium, low, and atmospheric pressure flash tanks along with vapors from the vacuum tank and demethanizer overheads get a second chance at recovery, after removal of $C_1$ or $C_2$ in second extraction unit 150 and rejection of $C_3$ and/or $C_4$ in de-ethanizer unit 170, through extractor 11 in all four of Cases VI through VIII. It is this key factor that allows the achievement of unusually high recoveries. This second chance at recovery for desirable hydrocarbons, while simultaneously rejecting intermediate-boiling hydrocarbons, provides another degree of freedom in process design that is not available in any of the natural gas liquids extraction processes described earlier.

Another important feature that is novel to this invention is that the rich solvent leaving the second extractor 151 in stream 155 does not contain more than the specification amounts of lighter undesirable hydrocarbons that are permitted in the final liquid product stream. It is more economical to recover slightly less amounts of heavier desirable components in second extracting unit 150 and recycle any unrecovered desirable heavier hydrocarbons to first extracting unit 10 for additional yield, while insuring that the lighter components present in rich solvent are within the allowance of combined liquid specification fluid. This result can be easily achieved by selecting the operating pressure of the second extracting unit 150 and adjusting the solvent flow rate to stream 141.

Another important element that is unique to this invention is the ability to select and set a pressure in each of the intermediate flashes from medium to vacuum tanks, based on economic objectives for a given stream. The pressures are chosen such that all undesirable components, after adjusting the solvent rate to first extractor 11 through line 55, are flashed off and directly recycled back to first extractor 11 or further processed in second extractor 151 while bypassing demethanizer 91 in order to recover desirable components in high yield. The feed-forward streams to demethanizer system 90 are composed primarily of desirable components for stream 95.

Controlling the pressure within demethanizer 91 and the temperature at the bottom of demethanizer 91 through reboiler 99, to obtain a primary separation of consecutively lower molecular weight hydrocarbons, plus a secondary separation in extractor unit 150 and a tertiary separation of extractives in de-ethanizer unit 170, also enables specific undesirable components to be selectively rejected, even though the rejected hydrocarbon or hydrocarbons are sandwiched between accepted components. Such accepted components are ethane, propane, butanes, or $C_5+$ depending upon the operational objectives and existing market conditions. Such rejected components are propane and/or butane.

The operating pressure of demethanizer unit 90 can also be varied at will, consistent with the operational objectives, thereby operating the same equipment as a de-ethanizer if $C_3+$ product is desired, as a depropanizer if $C_4+$ product is desired, or as a debutanizer if $C_5+$ product is desired, instead of using it as a demethanizer. The operating pressure in demethanizer unit 90 can vary from 50–450 psia.

Similarly, de-ethanizer unit 170 is operated as a de-ethanizer or as a depropanizer. The pressure of unit 170 can be varied at will. However, if ethane is to be rejected, such as for Case VII, it is simpler to do so with demethanizer 91 so that for most purposes de-ethanizer 171 must merely separate $C_3$ from $C_4$, as shown in Table I.

Another factor that allows unusually high hydrocarbon recoveries and a extremely flexible degree of component selectivity is essentially the recognition of relative gas solubility and loading capacity characteristics of the various physical solvents, such as DMPEG. Due to significant departures among the relative solubilities of ethane, propane, iso and normal butanes, iso and normal pentanes, hexane, heptane, etc., relative to methane, the desired hydrocarbons can be selectively recovered from a natural gas stream by adjusting the solvent flow rate to extractor units 10 and 150, recycling flashed gas mixtures to extractor 11, adjusting the operating pressure levels in the intermediate flash units 20,30,40,70, and operating temperature and pressure levels in demethanizer unit 90 and de-ethanizer unit 170.

Many customers for the residue natural gas, such as petrochemical plants manufacturing polyolefins and plastics therefrom, would like to have a feed stream containing certain desirable components, usually two or three of the lower molecular weight hydrocarbons. For example, a plant may specify a $C_2/C_3$ ratio of 70/30 by weight or by volume. As another example, a plant may wish to have $C_4$ and $C_1$, using the $C_1$ as the inert gas to provide a desired liquid or vapor hourly space velocity. The amount of diluent may be inconsequential, within broad ranges, and the presence of nitrogen would be equally as useful as methane for dilution purposes.

Other customers for a residue natural gas might specify the Btu content within certain ranges, such as 950 to 975 Btu/SCF or 1050 to 1075 Btu/SCF without requiring that the gas contain any particular hydrocarbons.

With this process, the residue natural gas can be adjusted selectively to provide any desired composition or Btu content according to customers' orders and with rapid flexibility as measurements are made on the streams in lines 12,29,175. For example, Case V would provide a residue natural gas containing $C_1$ and $C_3$, Case VI would provide a residue natural gas containing $C_1$ and $C_4$, Case VII would provide residue natural gas containing $C_1$, $C_2$, and $C_4$, and Case VIII would provide residue natural gas containing $C_1$, $C_3$, and $C_4$. A customer might wish to dehydrogenate $C_4$, for example, and wish to have $C_1$ as diluent or might wish to dehydrogenate $C_2$ and $C_4$ to make a combined olefin feedstream for a combined plastic product and also want $C_1$ as diluent, whereby the product of Case VII would be satisfactory.

The process of this invention therefore enables the operator to provide one customer with a stream of liquid hydrocarbons product and to provide another customer with a residue natural gas with desired Btu content and a third customer with a residue natural gas having only selected components in a specified relationship and to be able to change these product streams, at both ends of the plant, on a relatively short notice.

It is important to note that these product streams of liquid hydrocarbon products and residue natural gas can be provided from an inlet natural gas from any source, having any composition, and having any adulteration from water and sour gas materials that natural sources may contain.

The potential $C_2+$ recoveries, when operating the extraction plant for selectively treating sweet or sour natural gas with equal effectiveness, can readily be entered in a computer program. Similarly, the price and composition of the inlet natural gas stream and the prices of the components of the liquid product can be incorporated into the same program along with costs of plant operation for each process step, such as compression after flashing to a specific pressure. A computer can thereby make calculations immediately after entry of any changed conditions and then can print instructions for the operator, so that the extraction plant can always be operated at the optimum profit levels.

Because it will be readily apparent to those skilled in the art of treating natural gas that innumerable variations, modifications, applications, and extensions of the examples and principles hereinbefore set forth can be made without departing from the spirit and the scope of the invention, what is hereby defined as such scope and is desired to be protected should be measured, and the invention should be limited, only by the following claims.

What is claimed is:

1. In a continuous process for producing from an inlet natural gas stream a liquid hydrocarbon product of a selected composition, which is selectively adjustable to substantially any selected degree in accordance with market conditions, and a residue natural gas stream of pipeline quality that selectively includes ethane, propane, butanes, or propane plus butanes, said process comprising the following steps:
   a. selectively extracting a stream of hydrocarbons that are primarily heavier than methane from said natural gas stream with a physical solvent; and
   b. selectively rejecting a consecutively lowest molecular weight portion of said extracted stream, said rejected portion comprising, as its heaviest component, said propane or said butanes;

wherein, for all components heavier than said ethane, there exists a need for selectively rejecting any one or two selected hydrocarbons of consecutive molecular weight that are heavier than another recoverable and desirable lower molecular-weight hydrocarbon which may include said ethane, an improvement which enables said process to provide said liquid hydrocarbon product comprising only selected hydrocarbon components of said natural gas stream, said improvement comprising:
   A. selectively extracting, with said physical solvent in a second extraction step, hydrocarbons selected from the group consisting of ethane, propane, and butanes from said rejected portion of said step b to form a rich solvent stream;

B. flashing said rich solvent stream in at least one flashing stage to separate said selected hydrocarbons from said physical solvent; and C. de-ethanizing said selected hydrocarbons to form:
(1) an overhead product comprising said recoverable and desirable lower molecular-weight hydrocarbons, and
(2) a bottoms product comprising undesirable hydrocarbons.

2. The process of claim 1, wherein said Step a is performed by the following steps:

A. extracting said hydrocarbons that are primarily heavier than methane from said natural gas stream with said physical solvent at pipeline pressures and at a solvent flow rate sufficient to produce said remainder of said natural gas stream and a rich solvent stream containing said solvent and a selected $C_1+$ mixture of hydrocarbons;

B. successively flashing said rich solvent stream in a plurality of flashing stages at successively decreasing pressures to produce a plurality of successive $C_1+$ gas fractions, having successively lower methane contents, and successive liquid mixtures of said solvent and mixtures of hydrocarbons having successively lower methane contents; and C. regenerating the liquid mixture from the last stage of said flashing stages to produce said physical solvent for said extracting.

3. The process of claim 2, wherein said rejecting of said Step b of claim 1 is performed by utilizing at least one of the following operational procedures:

A. selectively varying said solvent flow rate with respect to the flow rate of said natural gas stream during said extracting of said Step A of claim 2 to adjust the composition of said rich solvent relative to selected components of the group consisting of ethane, propane, and iso and normal butanes;

B. selectively varying the flashing pressures of said successive flashing stages to adjust the compositions of said successive gas fractions and of said successive liquid mixtures relative to said selected components;

C. recycling at least the first of said successive $C_1+$ gas fractions to said extracting of said Step A of claim 2 in order to extract maximum quantities of said hydrocarbons that are primarily heavier than methane; and D. demethanizing at least the last of said successive $C_1+$ gas fractions to produce said remainder of said extracted stream, by:
(1) selectively varying the pressure of said demethanizing, and
(2) selectively varying the bottoms temperature of said demethanizing.

4. The process of claim 3, wherein said selectively extracting of said Step A of claim 1 comprises the following steps:

A. selectively extracting said rejected portion with a second portion of said regenerated physical solvent from said Step C of claim 2 to produce a gas stream, selected from the group consisting of methane, ethane, and propane, and a second rich solvent stream, comprising said physical solvent and at least two of the highest molecular weight components of said rejected portion;

B. flashing said second rich solvent stream to produce an overhead stream consisting of said highest molecular weight components and a bottom solvent stream; and C. de-ethanizing said overhead stream to produce:
(1) said ethane, said propane, or said ethane plus propane as an overhead product stream; and
(2) said propane, said butanes, or said propane plus butanes as a bottoms stream for said combining with said remainder of said natural gas stream.

5. The process of claim 4, wherein:
A. said extracting of said Step A of claim 2 is a first extracting;
B. said extracting of said Step A of claim 4 is a second extracting;
C. said physical solvent used for said first extracting is a first portion of said regenerated physical solvent of said Step C of claim 2; and
D. said physical solvent used for said second extracting is a second portion of said regenerated physical solvent of said Step C of claim 2.

6. The process of claim 5, wherein said bottom solvent stream from said Step B of claim 4 is combined with said liquid mixture remaining from said plurality of flashing stages, as set forth in said Step C of claim 2, to form the feed to said regenerating of said Step C of claim 2.

7. The process of claim 6, wherein said at least last of said successive $C_1+$ gas fractions of said Step D of claim 3 is compressed, cooled, and condensed for said demethanizing, said demethanizing being achieved by heating said condensed gas fraction to a selected bottoms temperature and at a selected pressure to remove an off-gas mixture from said last $C_1+$ gas fraction, said off-gas mixture comprising essentially all of said methane and selected amounts of ethane, propane, and butanes that are present in said at least last gas fraction.

8. The process of claim 7, wherein said inlet natural gas stream is selected from the group consisting of:
A. natural gas saturated with water;
B. natural gas at less than saturation with water;
C. sour natural gas;
D. sour natural gas which is pre-sweetened in gas phase with an aqueous amine solution;
E. sweet natural gas; and
F. dry natural gas.

9. The process of claim 8, wherein said residue natural gas contains less than 7 pounds of water vapor per million standard cubic feet as said selected degree.

10. The process of claim 9, wherein said physical solvent is selective toward ethane and heavier hydrocarbon components of said inlet natural gas stream over methane, such that the relative volatility of methane over ethane is at least 5.0 and the hydrocarbon loading capacity, defined as solubility of ethane in solvent, is at least 0.25 standard cubic feet of ethane per gallon of solvent.

11. The process of claim 10, wherein said physical solvent is selected from the group consisting of dialkyl ethers of polyalkylene glycol, N-methyl pyrrolidone, dimethyl formamide, propylene carbonate, sulfolane, and glycol triacetate.

12. The process of claim 11, wherein said solvent is selected from the group consisting of dimethyl ether of polyethylene glycol, dimethyl ether of polypropylene glycol, dimethyl ether of tetramethylene glycol, and mixtures thereof.

13. The process of claim 12, wherein said solvent is dimethyl ether of polyethylene glycol containing 3–10 ethylene units and having a molecular weight of 146 to 476.

14. The process of claim 13, wherein the flow rates of said physical solvent to said first extracting and to said second extracting are within the range of 0.001 to 0.5 gallon per standard cubic foot of feed to said extracting, said flow rates being dependent upon the pressures utilized for said first and second extracting.

15. The process of claim 14, wherein said first portion of said regenerated physical solvent varies within the range of 0.005 to 0.5 gallon per standard cubic foot of inlet natural gas feed to said first extracting.

16. The process of claim 15, wherein said second portion of said regenerated physical solvent varied within the range of 0.001 to 0.2 gallon per standard cubic foot of said rejected portion as feed to said second extracting.

17. The process of claim 16, wherein said regenerating is done by distillation.

18. The process of claim 17, wherein said regenerating is done by supplying heat to a reboiler to produce an overhead vaporous stream which is cooled, settled, pumped, and returned to said regenerator after disposing of excess waste water therefrom.

19. The process of claim 10, wherein said selected flashing pressures of said successive flashing stages vary between 1300 psia and 2 psia.

20. The process of claim 19, wherein said bottoms temperature of said demethanizing is varied between 0° F. and 300° F.

21. The process of claim 20, wherein said process is operated to recover $C_4+$ hydrocarbon liquids and to reject ethane and propane therein as said selected degree, said demethanizing being operated as depropanizing.

22. The process of claim 21, wherein said liquid product of said depropanizing comprises approximately 100% of the butanes and all heavier hydrocarbons in said natural gas stream and less than 2% of ethane and propane therein as said selected degree.

23. The process of claim 22, wherein said ethane and said propane are accompanied by a portion of said methane in said inlet natural gas stream to form an extraction feed stream for said second extracting of said Step A of claim 4.

24. The process of claim 23, wherein said extraction feed stream is produced entirely by said depropanizing of claim 21.

25. The process of claim 23, wherein said extraction feed stream is produced partly as at least one off-gas stream from said multiple flashing stages and partly as an overhead stream from said depropanizing of claim 21.

26. Said residue natural gas stream of claim 25, wherein said stream has a Btu content within a selected range.

27. Said residue natural gas stream of claim 26, wherein said stream has a composition selected from the group consisting of the following components:
 A. $C_1$ and $C_3$;
 B. $C_1$ and $C_4$;
 C. $C_1$, $C_2$, and $C_4$; and
 D. $C_1$, $C_3$, and $C_4$,
wherein said components are predominant.

28. Said residue natural gas stream of claim 25, wherein said stream has a specified composition of any selected degree and includes methane as a major or minor component.

29. Said residue natural gas stream of claim 28, wherein said stream has a composition selected from the group consisting of the following components:
 A. $C_1$ and $C_3$;
 B. $C_1$ and $C_4$;
 C. $C_1$, $C_2$, and $C_4$; and
 D. $C_1$, $C_3$, and $C_4$,
wherein said components are predominant.

30. Said liquid hydrocarbon product of claim 25, wherein said product has a composition selected from the group consisting of the following components:
 A. $C_2$ and $C_4+$;
 B. $C_2$, $C_3$, and $C_5+$;
 C. $C_3$ and $C_5+$; and
 D. $C_2$ and $C_5+$,
wherein said components are predominant.

31. The process of claim 20, wherein said process is operated to remove $C_5+$ hydrocarbon liquids from said natural gas stream and to reject ethane, propane, and the butanes therein as said selected degree, said demethanizing being operated as debutanizing.

32. The process of claim 31, wherein said liquid product of said debutanizing comprises approximately 100% of the pentanes and all heavier hydrocarbons in said natural gas stream and less than 2% of said ethane, said propane, and said butanes therein as said selected degree.

33. The process of claim 32, wherein said extraction feed stream for said second extracting comprises a portion of said $C_1$ component and essentially all of said $C_2$, $C_3$, and $C_4$ components thereof.

34. The process of claim 33, wherein said $C_2$, said $C_3$, and said $C_4$ are said highest molecular weight components of said overhead stream after said flashing according to said Step B of claim 4.

35. The process of claim 34, wherein said de-ethanizing is operated as depropanizing.

36. The process of claim 35, wherein said $C_2$ and said $C_3$ form said overhead stream from said depropanizing, said liquid hydrocarbon products consist essentially of said $C_2$, said $C_3$, and said $C_5+$ hydrocarbons, and said depropanizing bottoms consist essentially of said $C_4$ hydrocarbons.

37. The process of claim 34, wherein:
 A. said $C_2$ forms said overhead stream from said depropanizing;
 B. said depropanizing bottoms consist essentially of said $C_3$ and said $C_4$ hydrocarbons; and
 C. said liquid hydrocarbon products consist essentially of said $C_2$ and said $C_5+$ hydrocarbons.

38. The process of claim 31, wherein said extraction feed stream for said second extracting comprises a portion of said $C_2$ component and essentially all of said $C_3$ and $C_4$ components thereof.

39. The process of claim 38, wherein said $C_3$ and $C_4$ components in said gas stream of said Step A in claim 4 are said highest molecular weight components of said overhead stream of said Step B in claim 4.

40. The process of claim 39, wherein:
 A. said de-ethanizing is operated as depropanizing;
 B. said overhead product stream from said depropanizing consists of said $C_3$;
 C. said bottoms stream from said depropanizing consists of said $C_4$; and
 D. said liquid hydrocarbon products consist essentially of said $C_3$ and said $C_5+$ hydrocarbons.

41. In a continuous process, for separating hydrocarbons heavier than methane from an inlet natural gas stream and for producing a liquid hydrocarbon product having a composition which is selectively adjustable to substantially any selected degree in accordance with market conditions, which comprises:

a. extracting said hydrocarbons heavier than methane from said natural gas stream with a physical solvent at pipeline pressures and at a solvent flow rate sufficient to produce rich solvent containing a $C_1+$ mixture of hydrocarbons and a residue natural gas stream of pipeline quality which is returned to a pipeline, said solvent flow rate being selectively varied with respect to the flow rate and composition of said natural gas stream during said extracting in order to adjust the composition of said rich solvent relative to selected components of the group consisting of ethane ($C_2$), propane ($C_3$), and iso and normal butanes ($C_4$);

b. successively flashing said rich solvent in a plurality of flashing stages at successively decreasing pressures in order to produce a plurality of successive $C_1+$ gas fractions, having successively lower methane contents, and liquid mixtures of said solvent and mixtures of hydrocarbons having successively lower methane contents, the flashing pressures of said successive flashing stages being varied in order to adjust the compositions of said successive gas fractions and of said successive liquid mixtures relative to said selected components;

c. regenerating the liquid mixture from the last stage of said flashing stages in order to produce said physical solvent for said extracting;

d. recycling at least the first of said successive flashed $C_1+$ gas fractions to said extracting in order to extract maximum quantities of said ethane and heavier hydrocarbons ($C_2+$); and e. stripping at least the last of said successive $C_1+$ gas fractions, in order to produce said liquid hydrocarbon product comprising said selected components and a recycle gas stream comprising $C_1$, $C_1+C_2$, $C_1+C_2+C_3$, or $C_1+C_2+C_3+C_4$ for recycle to said extracting, by:

(1) selectively varying the pressure of said stripping and (2) selectively varying the bottoms temperature of said stripping, wherein, for all components heavier than said ethane, there exists a need for selectively rejecting any one or two selected hydrocarbons of consecutive molecular weight that are heavier than another recoverable and desirable lower molecular-weight hydrocarbon which may include said ethane, the improvement which enables, to any selected degree:

(1) selected $C_2+$ components to be extracted from said recycle gas stream, (2) at least one intermediate component, selected from the group consisting of said $C_3$ and said $C_4$, to be combined with said residue natural gas stream, and (3) other selected components of said recycle gas stream to be combined to any selected degree with said liquid hydrocarbon product, said improvement comprising:

A. extracting an extract feed stream, selected from the group consisting of said recycle gas stream, a flashed-off gas stream from at least one of said plurality of flashing stages, and mixtures of said gas stream, with said physical solvent at a selected flow rate that controls the selected degree of recovery of said selected $C_2+$ components in a rich solvent stream, the unextracted portion of said extract feed stream being recycled to said extracting of said inlet natural gas stream of said Step a.

B. flashing said rich solvent stream and producing at least a singly flashed-off gas stream, containing said selected $C_2+$ components, and a bottoms solvent stream for recycle to said regenerating; and C. splitting said singly flashed-off gas stream and producing an overhead product stream, selected from the group consisting of $C_2$, $C_3$, and $C_2+C_3$, and a bottoms stream, selected from the group consisting of $C_3$, $C_4$, and $C_3+C_4$, said bottoms stream being combined with said residue natural gas stream of said Step a and said overhead product stream being combined with said liquid hydrocarbon product of said Step e.

42. The process of claim 41, wherein:

A. said extracting of said natural gas stream is a first extracting;

B. said extracting of said Step A is a second extracting;

C. said physical solvent used for said first extracting is a first portion of said regenerated physical solvent; and D. said physical solvent used for said second extracting is a second portion of said regenerated physical solvent.

43. The process of claim 42, wherein said bottoms solvent stream from said Step G of claim 36 is combined with said liquid mixture remaining from said plurality of flashing stages of said Step B of claim 36 to form the feed to said regenerating.

44. The process of claim 43, wherein said inlet natural gas stream is selected from the group consisting of:

A. natural gas saturated with water;

B. natural gas at less than saturation with water;

C. sour natural gas;

D. sour natural gas which is pre-sweetened in gas phase with an aqueous amine solution;

E. sweet natural gas; and

F. dry natural gas.

45. The process of claim 39, wherein said physical solvent is selective toward ethane and heavier hydrocarbon components of said inlet natural gas stream over methane, such that the relative volatility of methane over ethane is at least 5.0 and the hydrocarbon loading capacity, defined as solubility of ethane in solvent, is at least 0.25 standard cubic foot of ethane per gallon of solvent.

46. The process of claim 45, wherein said physical solvent is selected from the group consisting of dialkyl ethers of polyalkylene glycol, N-methyl pyrrolidone, dimethyl formamide, propylene carbonate, sulfolane, and glycol triacetate.

47. In the recovery of hydrocarbon liquids from a hydrocarbon gas stream with a physical solvent, wherein a need exists for flexibly recovering said liquids in any selectivity and according to any combination, including the selective rejection of one hydrocarbon component of said recovered liquids that is heavier than another recovered hydrocarbon component thereof, the improvement comprising:

A. selective extraction of a gas stream containing $C_1$–$C_4$ hydrocarbons with a lean physical solvent to produce a rich solvent stream containing $C_2$–$C_4$ hydrocarbons, said physical solvent being selective toward ethane and heavier hydrocarbon components of said gas stream such that the relative volatility of methane over ethane is at least 5.0 and the hydrocarbon loading capacity, defined as solubility of ethane in solvent, is at least 0.25 standard cubic feet of ethane per gallon of solvent;

B. flashing said rich solvent stream to produce said lean solvent stream and a $C_2$–$C_4$ hydrocarbons stream;

C. de-ethanizing said $C_2$–$C_4$ hydrocarbons stream to produce an overhead product stream, selected from the group consisting of $C_2$, $C_3$, and $C_2+C_3$ hydrocarbons, and a bottoms stream, selected from the group consisting of $C_3$, $C_4$, and $C_3+C_4$ hydrocarbons; and D. recycling said lean solvent stream of said Step B to said Step A.

* * * * *